US005698069A

United States Patent [19]

Aiyer et al.

[11] Patent Number: 5,698,069

[45] Date of Patent: Dec. 16, 1997

[54] TECHNIQUE FOR DETECTING PARTICLES ON A WAFER SUPPORT SURFACE

[75] Inventors: Arun A. Aiyer, Fremont; Kyoichi Suwa, San Mateo, both of Calif.

[73] Assignee: Nikon Precision Inc., Belmont, Calif.

[21] Appl. No.: 764,664

[22] Filed: Dec. 11, 1996

Related U.S. Application Data

[63] Continuation of Ser. No. 525,278, Sep. 10, 1995, abandoned.
[51] Int. Cl.$^6$ ................................................ H01L 21/00
[52] U.S. Cl. ........................ 156/626.1; 216/60; 216/85
[58] Field of Search ........................ 156/626.1, 662.1, 156/657; 206/59, 40, 60, 84, 58; 437/8

[56] References Cited

U.S. PATENT DOCUMENTS 4,167,337  9/1979  Jäerisch et al.

FOREIGN PATENT DOCUMENTS

| 49-63458 | 6/1974 | Japan . |
| 2210624 | 9/1987 | Japan ................... 156/626.1 |
| 2-400-207 | 7/1992 | Japan . |

*Primary Examiner*—William Powell
*Attorney, Agent, or Firm*—Bennet K. Langlotz

[57] ABSTRACT

A method of detecting particles on a wafer support surface comprising positioning a wafer in a first position on the surface with the wafer in the first position, generating a first pattern on the wafer, and moving the wafer. Then, after moving the wafer, generating a second pattern on the wafer to generate a moiré pattern by the interaction of the second pattern with the first pattern. The moiré pattern is inspected to identify any visual distortion in the moiré pattern due to physical distortion of the wafer caused by a particle on the support surface during the generation of the first pattern. The patterns may be ruled parallel lines, and the second pattern may be moved during inspection to shift the moiré pattern to reveal distortions over a wide area.

28 Claims, 3 Drawing Sheets

TECHNIQUE FOR DETECTING PARTICLES ON A WAFER SUPPORT SURFACE

This application is a continuation of application Ser. No. 08/525,278, filed on Sep. 8, 1995, now abandoned.

FIELD OF THE INVENTION

This disclosure relates to semiconductor microlithography, and more particularly to inspection techniques for detecting contaminant particles on imaging equipment.

BACKGROUND AND SUMMARY OF THE INVENTION

A primary objective of photo microlithography is to create images of the finest detail possible. High resolution images having extremely narrow line and space widths permit manufacture of complex integrated circuits on chips of small size. With the fine details required, even small unwanted variations and distortions may be unacceptable.

In production of semiconductor chips, a wafer is positioned on a flat support surface or stage, and an image of a mask is projected onto the wafer to generate a permanent image that is revealed by chemical processing. If a microscopic particle is trapped on the support surface below the wafer, it may distort the wafer, and thereby distort the resulting image. A particle will normally cause the localized area of the wafer to bow upward, causing the upper surface of the wafer to stretch slightly. An image projected onto the stretched area will then contract when the wafer is removed from the support surface and allowed to return to its relaxed state. The bowing may also cause localized defocusing of the image.

Because the particles that may cause these distortions are too small to be readily detected by conventional means, it is necessary to conduct occasional tests for contamination to indicate when cleaning of the support surface is needed.

A current method of detecting contaminant particles is to print a reference grating onto a test wafer, to process the wafer to generate a permanent image of the grating, and to inspect the resulting image. The inspection is done with uniform illumination, and a diffraction effect may help to reveal some variations in the line widths or spacings. However, this technique has limited effectiveness for detecting the smaller particles that may cause unacceptable distortions in some of the finest microlithographic applications.

These limitations are reduced or avoided by providing a method of detecting particles on a wafer support surface comprising positioning a wafer in a first position on the surface with the wafer in the first position, generating a first pattern on the wafer, and moving the wafer. Then, after moving the wafer, generating a second pattern on the wafer to generate a moiré pattern by the interaction of the second pattern with the first pattern. The moiré pattern is inspected to identify any visual distortion in the moiré pattern due to physical distortion of the wafer caused by a particle on the support surface during the generation of the first pattern. The patterns may be ruled parallel lines, and the second pattern may be moved during inspection to shift the moiré pattern to reveal distortions over a wide area.

DETAILED DESCRIPTION OF A PREFERRED EMBODIMENT

Figure 1:
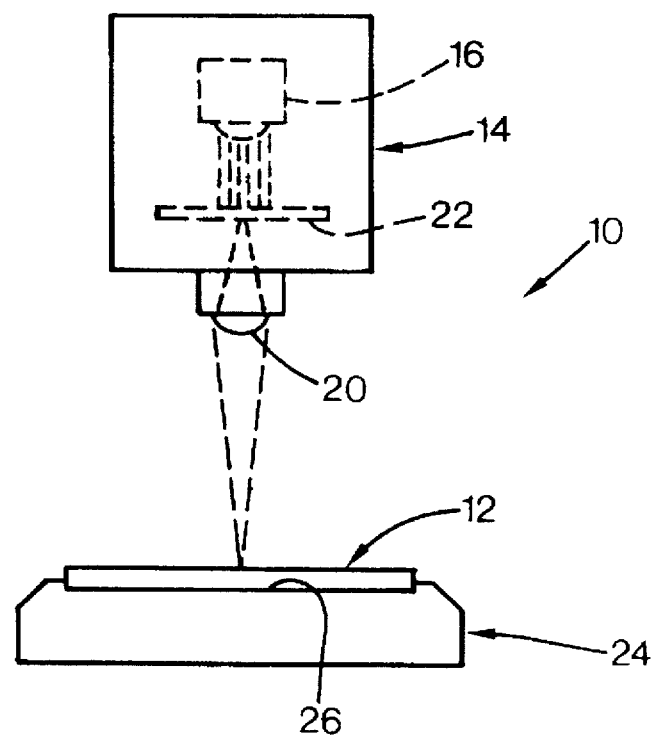
FIG. 1 is a simplified side view of a stepper operable according to a preferred embodiment of the invention.

FIG. 1 shows a stepper 10 for photolithographic imaging of detailed images on the surface of a semiconductor wafer 12. The stepper includes a projector assembly 14 that includes a light source 16 and a projector lens 20. A removable reticle or mask 22 carrying an image of transparent and opaque portions is positioned within the projector assembly.

A stage or wafer support element 24 having a flat wafer support surface 26 facing the lens 20 is positioned below the lens so that the wafer 12 resting on the surface may be imaged by the lens. The wafer support 24 is movable in X and Y axes in the plane of the surface 26. Thus, the wafer may be "stepped" so that multiple images of integrated circuits may be imprinted on a single wafer as the lens 20 focuses the image of the mask at a reduced scale. The wafer support may include an array of small holes (not shown) through the surface 26 in communication with a vacuum pump (not shown) to securely draw the entire wafer against the surface to ensure accurate focus.

Figure 2:
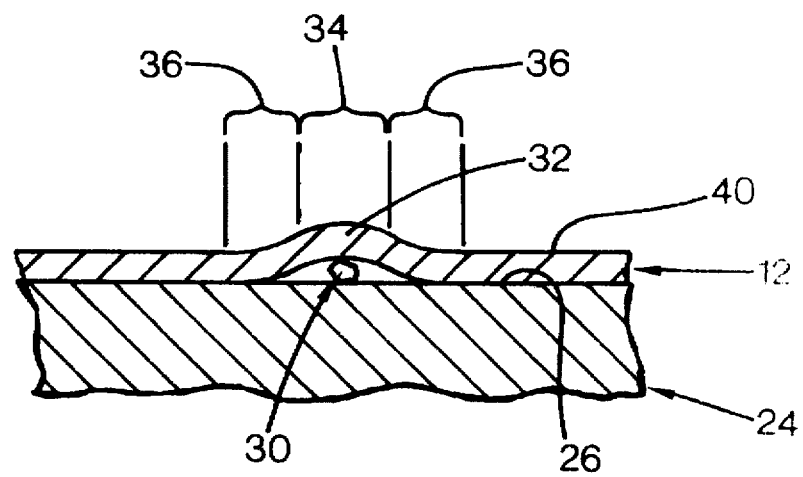
FIG. 2 is an enlarged sectional view of a portion of the stepper of FIG. 1.

As shown in exaggerated scale in FIG. 2, a contaminant particle 30 may become trapped between the wafer 12 and the support surface 26. Although the wafer is generally rigid, it is still prone to some flexing due to the particle. Thus, a bulge 32 develops over the particle, as the surrounding region is drawn to the support surface by gravity and/or by suction. A typical wafer bulge caused by a point-like particle has two regions: a central convex region 34, and a surrounding annular concave skirt region 36. The central region has a positive curvature, so that the upper surface 40 of the wafer is stretched to form the convex shape. The annular skirt has a negative curvature, so that the upper surface is compressed at the skirt. If an elongated fiber or needle-like shard contaminates the surface, the cross sectional view of FIG. 2 would be the same, although the bulge in part would be a convex cylindrical section, and bounded on each major edge by a convex cylindrical section.

After an image is projected and imprinted onto the wafer when a particle 30 is present, the imprinted image changes when the wafer is removed from the support 24. Because particle-generated strains are within the elastic range of semiconductor materials, the wafer returns to a flat state after removal from the stage. When this occurs, the scale of the image in the central region 34 shrinks as the stretched surface returns to its natural state. Conversely, the scale of the image in the skirt region 36 expands as the compressed surface relaxes. While the image retains its proper proportions when the wafer is flexed over a particle (aside from focus errors), the image scale is locally distorted when the wafer is removed for further processing and use.

Although the wafer support surface is maintained in a clean environment, and may be frequently cleaned to remove most particles, some particles may remain undetected. A test procedure is employed occasionally to confirm whether particles have been deposited on the surface, such as by the shedding of microscopic fragments of prior wafers processed. The test procedure may be used frequently to indicate the presence of a particle soon after it occurs, minimizing the amount of defective production. Alternatively, the test may be conducted at longer intervals, such as at labor shift changes or when batch carriers of multiple wafers are removed from the stepper for further processing. This latter approach is suitable for when contaminant particles occur only rarely. Also, when an end-of-shift test procedure shows that a contaminant particle became present during a shift, the location of the particle may be noted. Then, instead of scrapping all production from that shift, only those integrated circuits affected by the distortion need be marked as defective, with the remainder on each wafer being retained as unaffected.

The preferred test procedure entails printing a test pattern on a test wafer resting in the normal matter on the support surface, removing the test wafer to an uncontaminated surface, and illuminating, printing, or overlaying the printed wafer with a similar inspection pattern to generate a moiré pattern as the test pattern and inspection pattern visually interfere.

Figure 3:
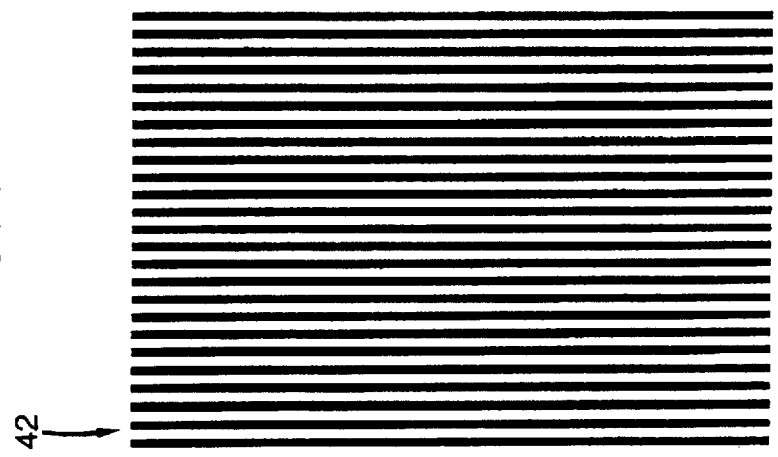
FIG. 3 is an enlarged plan view of a first test pattern according to the preferred embodiment of the invention.

FIG. 3 shows the test pattern 42, which is an array of parallel lines each having a width equal to half the pitch or center-to-center spacing. Thus the line widths equal the space widths. In the preferred embodiment, the line width on the wafer is preferably in the range of 0.5 to 1.0 μm; because the reduction lens reduces the mask image by a factor of 4, the mask may have a line width of about 2 to 4 μm. A wide range of values outside of these ranges may be suitable for certain applications without departing from the principles of the invention. The test pattern may cover the entire wafer, or may cover only a patch having the area of a single integrated circuit chip on the wafer, in which case the test image is stepped to cover substantially the entire wafer in a matrix of adjacent patches.

Figure 4:
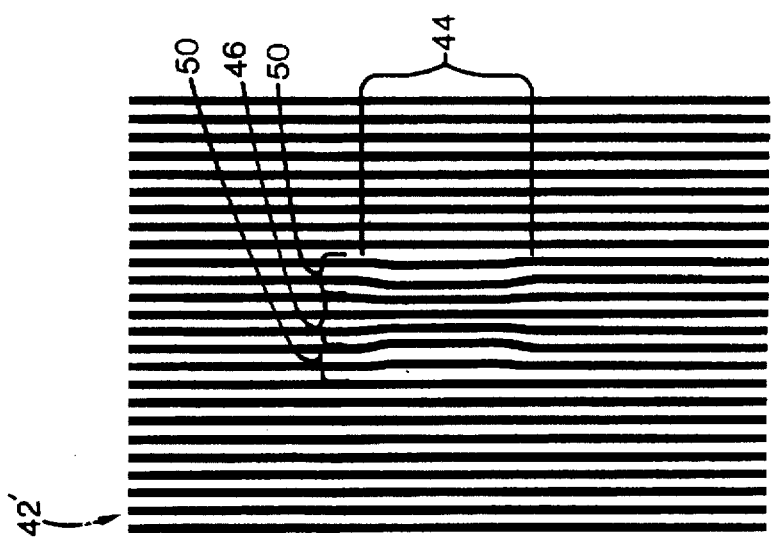
FIG. 4 is an enlarged plan view of a distorted test pattern according to the preferred embodiment of the invention.

FIG. 4 shows a portion of the test wafer that has been imaged over an elongated particle, then removed from the wafer support to a flat, unstressed position, yielding the illustrated distorted test pattern 42'. In this distortion example the contaminant particle causes a distortion zone 44 to be generated. The distortion zone has a central zone portion 46 positioned immediately over the particle and equivalent to the formerly convex region 34. A pair of flanking peripheral zone portions 50 are equivalent to the formerly concave regions 36. For simplicity, the distorted portion of the pattern is shown as oblong, although in many cases it may be circular. What is shown is a useful model for any type of particle-generated distortion.

Figure 5:
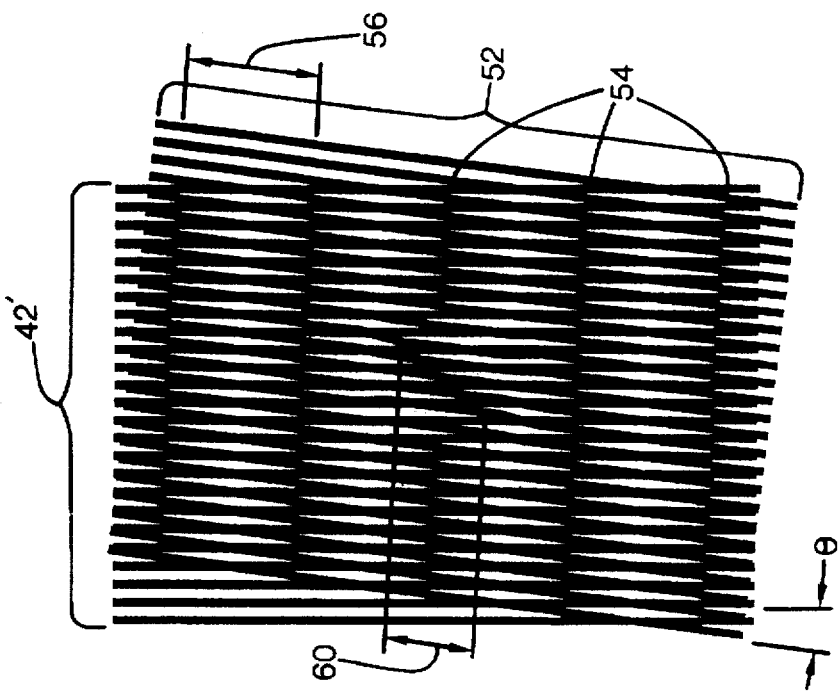
FIG. 5 is an enlarged plan view of a moiré pattern according to the preferred embodiment of the invention.

In FIG. 5, the distorted test pattern has been overlaid with an inspection pattern 52 to generate a moiré pattern appearing as broad parallel stripes or fringes 54. The inspection pattern has the same line width and pitch as the test pattern 42, and covers the entire test pattern for inspection of substantially the entire wafer. To generate the moiré pattern, the inspection pattern is angularly offset slightly from the test pattern by angle θ, which may range from 0° and up, preferably a small acute amount. With θ being a small angle, the moiré fringes are spaced apart by a distance 56 equal to the pitch of the patterns divided by θ (in radians). The fringe spacing preferably ranges between about 5 and 15 mm for convenient visibility, with other wide ranges being potentially useful for other applications.

The moiré fringe passing over the distortion zone 44 is noticeably distorted to form a jog or zig-zag. The jog appears approximately as a single complete sine or sawtooth wave having an amplitude 60 that is sufficient to be readily visible, even when the distortion 44 may not be. The offset amount of any line in the distortion zone from where the line should be may be expressed as an offset "d". This will be greatest in the example at the boundaries between the central zone portion 46 and the peripheral zone portions 50. The amplitude 60 of the moiré jog may be calculated as the maximum offset d divided by θ.

In the preferred embodiment, the spacing of the test and inspection patterns is identical, and the offset angle θ is a small non zero amount. In alternative embodiments, the pitch of the patterns might be different, with a zero offset angle, providing moiré fringes parallel to the pattern lines instead of perpendicular. Even a perfectly aligned inspection pattern that is a negative image of the test pattern would reveal distortions; all undistorted printed lines or other images would just be revealed by the inspection pattern, while any offset would be visible as revealed portions of the spaces between the printed lines.

Using a static version of the above technique, the inspection pattern may be fixed relative to the test pattern. This may be achieved by reprinting the test pattern after shifting the wafer on the support surface or by rotating the wafer by 180°+θ°. Although the distorting particle would still remain on the support surface, the affected portion of the wafer would be moved to another, presumably flat portion of the surface. This would create a second moiré distortion where the inspection pattern was distorted by the particle. After both patterns are imaged, the wafer may be processed for inspection.

The static technique must weigh a tradeoff between a small θ, which generates widely spaced moiré fringes and a large jog amplitude magnification for detection of the smallest distortions, and a larger θ, which narrows the fringe spacing to reduce the risk that a small localized distortion would be undetectable if it aligned in the space between fringes. To avoid the limitations of this trade off, a dynamic technique may be used.

The dynamic technique permits the use of very small θ values to provide high detection sensitivity, and avoids concealed distortions by moving the inspection pattern 52 relative to the test pattern 42' during inspection. Movement of the inspection pattern generates movement of the moiré fringes, which sweep over the wafer to reveal distortions at any location. By moving the inspection pattern 52 by a distance equal to the pitch of the pattern lines in a direction perpendicular to the pattern lines, the moiré pattern shifts perpendicularly to the direction of its fringes by an amount equal to the pitch of the fringes. Thus, only a small movement is required to scan the entire wafer. The movement should be at a slow constant velocity to provide visibility of distortions. The shifted pattern may be moved so that it passes over the stationary pattern lines with a frequency preferably in the range of 0.5 to 1.0 Hertz.

Movement of the inspection pattern may be provided any of several ways. A ruled glass grating may be directly overlaid onto the imaged wafer and either the grating or wafer moved. Or, the wafer may be illuminated with a projected image of the inspection pattern, which may be moved, or held stationary while the wafer moves.

Figure 6:
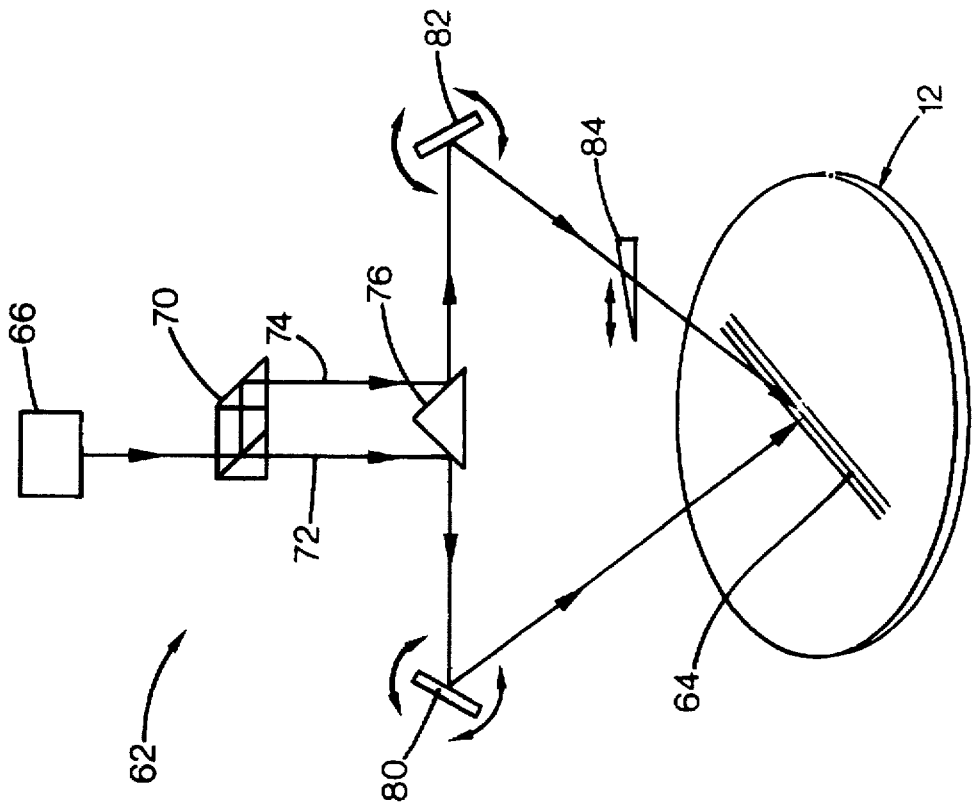
FIG. 6 is a schematic view of a first alternative embodiment of the invention.

FIG. 6 shows an inspection pattern generator 62 that generates a swath 64 of parallel illuminated lines having the same pitch as the test pattern. The swath is preferably wide enough to cover the entire wafer, or may cover a smaller subsection of the wafer that is large enough to view several fringe lines. Alternatively, the swath may be a narrower stripe that is rapidly and repeatedly scanned over the wafer in the manner of a rasterized video image to create the impression of a broad pattern of parallel lines covering the entire wafer 12.

A laser diode 66 provides a light source that emits a beam toward a beam splitter and mirror assembly 70 that split the beam into two parallel beam segments 72 and 74. The beam segments are directed to different faces of a mirror assembly 76, which diverts the beam segments in opposite colinear directions parallel to the wafer, each to a steerable and movable mirror 80, 82. Each mirror 80, 82 directs the respective beam segment onto the swath 64 of the wafer, with the optical interference of the beam segments generating interference lines having the desired pitch. The beam segments are directed at the wafer from different positions and directions to generate the interference lines of the second pattern. By moving the steerable mirrors 80, 82 along the beam segment paths parallel to the wafer, the position of the swath may be swept across the wafer.

To provide a dynamically moving inspection pattern, the phase of the second beam segment 74 is shifted by a moving transparent optical wedge 84 with in the path of the segment. This creates a changing phase differential between the beam segments 72, 74. By moving the wedge so that the thickness through which the beam passes is changing, the path length or phase of the beam segment 74 is increasingly altered relative to that of beam segment 72. The wedge must be sufficiently large to permit it to be moved continuously during the time a wafer is inspected. The wedge may be reciprocated back and forth to provide a similar apparent reciprocating motion of the inspection pattern and the moiré fringes.

The continuing phase shift may also be considered as a frequency shift, since the increasing (or decreasing) thickness of the moving glass wedge through which the beam passes is equivalent to an increasing (or decreasing) distance over which the beam must travel. Thus, the continually changing phase generates a Doppler shift that effectively changes the frequency while the wedge is in motion.

Figure 7:
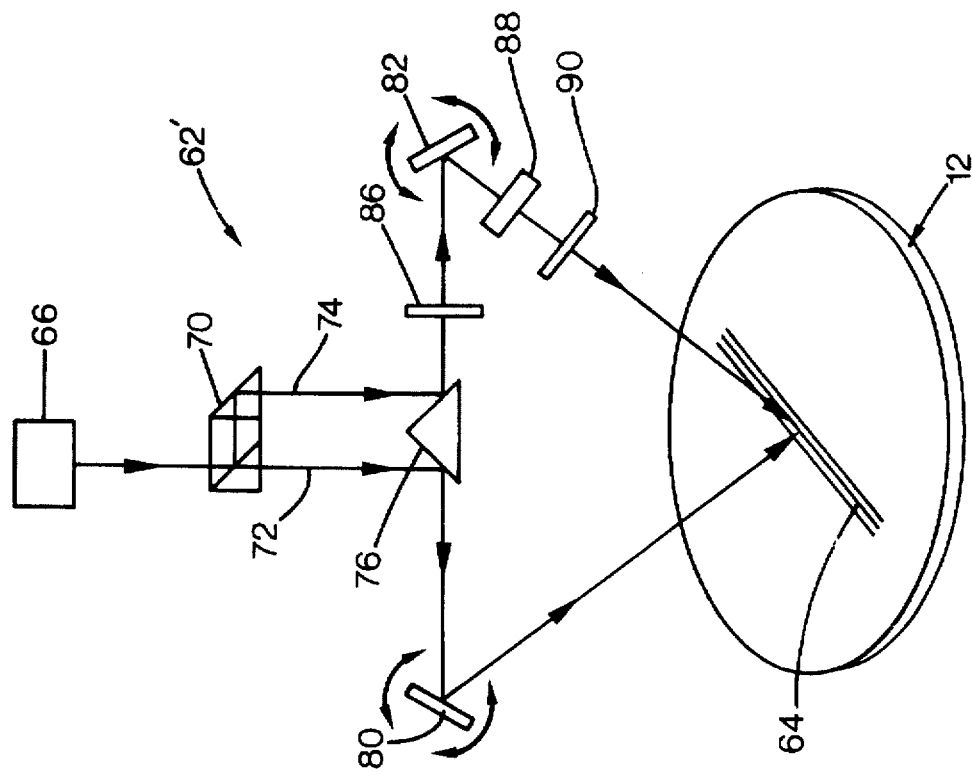
FIG. 7 is a schematic view of a second alternative embodiment of the invention.

FIG. 7 shows a variation on the apparatus of FIG. 6, with the wedge 84 replaced by an alternative means for shifting the frequency of beam segment 74. A quarter wave plate 86 is positioned in the beam path 74 between mirrors 76 and 82, a rotatable half wave plate 88 is positioned in the path after the mirror 82, and a quarter wave plate 90 is positioned after the half wave plate. The half wave plate 88 is rotated on an axis aligned with the path of the beam passing through it. The rate of rotation may be set at a frequency equal to one half of the desired frequency shift, which corresponds to the frequency of the motion of the moiré fringes.

While the above invention is described in terms of a preferred embodiment, the invention is not intended to be so limited.

We claim:

1. A method of detecting particles on a wafer support surface comprising:

positioning a wafer in a first position on the surface;

with the wafer in the first position, generating a first pattern on the wafer;

moving the wafer;

after moving the wafer, generating a second pattern on the wafer to generate a moiré pattern by the interaction of the second pattern with the first pattern; and inspecting the moiré pattern to identify any visual distortion in the moiré pattern due to physical distortion of the wafer caused by a particle on the support surface during the generation of the first pattern.

2. The method of claim 1 wherein positioning the wafer in the first position comprises flexing a first portion of the wafer over a particle on the support surface, and wherein moving the wafer comprises moving the first portion of the wafer away from the particle, such that the first portion is in an unflexed state during generation of the second pattern.

3. The method of claim 1 wherein the step of generating the second pattern comprises regenerating the first pattern offset at an angle from the original first pattern.

4. The method of claim 3 wherein the offset angle is less than 0.10 degrees.

5. The method of claim 1 wherein the step of generating the second pattern comprises generating an array of parallel lines.

6. The method of claim 5 wherein the step of generating the second pattern comprises overlaying a ruled grating on the wafer.

7. The method of claim 5 wherein the step of generating the second pattern comprises projecting light through a mask imprinted with the second pattern.

8. The method of claim 5 wherein the step of generating the second pattern comprises projecting light of different optical characteristics to generate an interference pattern of parallel lines.

9. The method of claim 8 wherein the step of projecting light comprises splitting a laser beam into two components, shifting the frequency of one of the components relative to the other component, and projecting both components onto the wafer.

10. The method of claim 8 wherein the step of projecting light comprises splitting a laser beam into two components, shifting the phase of one of the components relative to the other component, and projecting both components onto the wafer.

11. The method of claim 1 including generating the first pattern photolithographically.

12. The method of claim 1 including moving the second pattern relative to the first pattern during the step of inspecting the moiré pattern.

13. The method of claim 12 wherein moving the second pattern comprises moving a ruled grating across the wafer.

14. The method of claim 12 wherein the second pattern includes an array of parallel lines, and the step of moving the second pattern comprises moving the second pattern in a direction offset at an angle from the lines.

15. The method of claim 14 wherein moving the second pattern comprises moving the second pattern in a direction perpendicular to the lines.

16. The method of claim 12 wherein moving the second pattern comprises projecting light of two beams of light onto the wafer and changing the optical characteristics of one of the beams to generate a moving interference pattern.

17. A method of detecting particles on a wafer support surface comprising:

positioning a wafer in a first position on the surface;

with the wafer in the first position, generating a first pattern of parallel rulings on the wafer;

moving the wafer from the support surface;

after moving the wafer, generating a second pattern of parallel rulings on the wafer to generate a moiré pattern by the interaction of the second pattern with the first pattern;

moving the second pattern relative to the first pattern to shift the moiré pattern; and while moving the second pattern, inspecting the moiré pattern to identify any visual distortion in the moiré pattern due to physical distortion of the wafer caused by a particle on the support surface during the generation of the first pattern.

18. The method of claim 17 wherein generating the first pattern comprises printing an image on the wafer.

19. The method of claim 17 wherein generating the second pattern comprises overlaying a ruled transparent grating on the wafer.

20. The method of claim 17 wherein moving the second pattern comprises sliding the grating over the wafer.

21. The method of claim 17 wherein generating the second pattern comprises projecting light through a mask onto the wafer.

22. The method of claim 17 wherein generating the second pattern comprises projecting light of two different wavelengths onto the wafer.

23. The method of claim 17 wherein generating the second pattern comprises splitting a beam of light into a first component and a second component, shifting the frequency of one of the beam components, and projecting the beam components onto the wafer.

24. The method of claim 23 including passing one of the beam components through a rotating fractional wave plate.

25. The method of claim 23 including passing one of the beam components through a moving prism.

26. The method of claim 17 wherein the second pattern has the same pitch as the first pattern.

27. The method of claim 17 wherein the second pattern is offset at an acute angle from the first pattern.

28. The method of claim 17 wherein generating the second pattern comprises projecting light of two different wavelengths onto the wafer.

* * * * *